United States Patent
Sarstedt et al.

[11] Patent Number: 6,096,006
[45] Date of Patent: Aug. 1, 2000

[54] BLOOD-COLLECTION NEEDLE-DISPOSAL SYSTEM

[75] Inventors: Walter Sarstedt, Nümbrecht, Germany; Youcef Amokrane, Gyf sur Yvett, France

[73] Assignee: Sarstedt AG & Co., Numbrecht, Germany

[21] Appl. No.: 08/963,972

[22] Filed: Nov. 4, 1997

[30] Foreign Application Priority Data

Nov. 5, 1996 [DE] Germany ............... 196 45 514

[51] Int. Cl.⁷ .................. A61M 5/00; A61M 5/32
[52] U.S. Cl. .................. 604/110; 604/232; 604/192
[58] Field of Search ............... 604/187, 110, 604/162, 163, 167, 171, 192, 194, 195, 197, 198, 199, 200, 201, 205, 232, 240, 263, 243, 411–414, 413; 128/919

[56] References Cited

U.S. PATENT DOCUMENTS

| | | |
|---|---|---|
| 4,968,304 | 11/1990 | Alter . |
| 5,085,640 | 2/1992 | Gibbs ............ 604/110 |
| 5,120,310 | 6/1992 | Shaw ............ 604/195 |
| 5,188,613 | 2/1993 | Shaw ............ 604/111 |
| 5,290,256 | 3/1994 | Weatherford et al. ........ 604/198 |
| 5,387,195 | 2/1995 | Hicks ............ 604/192 |
| 5,403,289 | 4/1995 | Berrebi et al. ........... 604/198 |
| 5,522,804 | 6/1996 | Lynn ............ 604/187 |
| 5,527,285 | 6/1996 | Lenz et al. ........... 604/195 |
| 5,562,625 | 10/1996 | Stefanci . |
| 5,562,635 | 10/1996 | Whisson ............ 604/195 |
| 5,759,177 | 6/1998 | Whisson ............ 604/195 |
| 5,762,633 | 6/1998 | Whisson ............ 604/187 |
| 5,810,775 | 9/1998 | Shaw ............ 604/195 |

FOREIGN PATENT DOCUMENTS

| | | |
|---|---|---|
| 430 159 | 6/1991 | European Pat. Off. . |
| 602 882 | 6/1994 | European Pat. Off. . |
| 29 48 653 | 6/1981 | Germany . |
| 30 49 503 | 7/1982 | Germany . |
| 88 02 080 | 5/1988 | Germany . |
| 91 09 584 | 11/1991 | Germany . |
| WO92/202 81 | 11/1992 | WIPO . |

OTHER PUBLICATIONS

"Special Report and Product Review"(Health Devices, pp. 170–173, May 1991, vol. 20, No. 5).

*Primary Examiner*—Sharon Finkel
*Attorney, Agent, or Firm*—Herbert Dubno; Andrew Wilford

[57] ABSTRACT

A blood-collection apparatus has a needle having a sharp front end and a sharp rear end, a mounting collar on the needle between its ends and a holder tube extending along an axis and having front and rear ends. A piston axially slidable in the holder tube is provided with a mount adapted to fit complementarily with the mounting collar with the needle rear end directed axially back in the tube. The piston normally is at the tube front end with its mount projecting axially forward from the tube. A flexible strand has a front end attached to the piston and a rear end projecting from the tube rear end. This mount is fitted into the needle's collar after the blood-collection operation is complete so that a pull on the strand retracts the piston back into the tube carrying the needle fitted to its mount.

6 Claims, 1 Drawing Sheet

BLOOD-COLLECTION NEEDLE-DISPOSAL SYSTEM

FIELD OF THE INVENTION

The present invention relates to a blood-collection needle system. More particularly this invention concerns a method and apparatus for disposing of a needle of a blood-collection system.

BACKGROUND OF THE INVENTION

A standard blood-collection system such as described in German patents 2,948,653 and 3,049,503 of W. Sarstedt comprises a double-pointed needle and a generally tubular holder into whose front end a collar mounted on the needle between its points can be mounted so that the front end of the needle projects from the front end of the holder and the rear end of the needle projects back into the holder. A blood-collection vial with a pierceable cap can fit inside the holder. Thus to draw blood the front end of the needle is poked into a vein so that flow through the needle is established, possible by use of a syringe temporarily connected to the needle. Then the needle, while still in the vein, is fitted to the holder and a collection vial is pressed into the rear end of the holder so that the rear end of the needle pierces its cap and blood can flow into the vial. Several such vials can be filled this way, as is necessary for performing complex blood work.

Once the necessary amount of blood is drawn and the filled vials have been set aside, the needle is pulled out of the vein and normally must be capped in accordance with procedures described, for instance in "Special Report and Product Review" (*Health Devices*, p. 169ff, May 1991, vol 20, no. 5). In some situations the tubular holder can be reused and it is known to provide a separate large casing into which the entire needle assembly can be fitted when it is no longer needed. Either way it is absolutely essential to avoid needlesticks so that both ends of the needle itself have to be capped for disposal. Such capping is a problem and presents in itself a chance of needlestick to a technician who does not accurately fit the needle to the protective cap, normally the one it is delivered with. The classic needlestick accident is for the technician to stick the needle into the hand holding the protective cap it is being fitted to.

Other syringe systems are known from European patents 0,430,159 of J. Odenthal and 0,602,882 of J. Bell as well as from German Utility Model 91 09 584 assigned to U. Demuth which have a piston specially constructed that it can be coupled to the rear end of the needle assembly. Thus once the injection is complete, the piston is pushed fully forward and normally twisted to couple it to the needle, then the piston is pulled back to retract the needle into the body of the syringe, where it is protected. Such a system is usable for injections since the syringe is essentially empty when the injection is completed so that the piston is fully forward where it can be coupled to the rear end of the needle collar. In a blood-collection system, however, the vial is full and often does not even have a piston, so that this system is not usable.

OBJECTS OF THE INVENTION

It is therefore an object of the present invention to provide an improved needle for a blood-collection system.

Another object is the provision of such an improved needle for a blood-collection system which overcomes the above-given disadvantages, that is which can be easily rendered safe once it is no longer needed.

A further object is to provide an improved method of operating such a blood-collection needle.

SUMMARY OF THE INVENTION

A blood-collection apparatus has a needle having a sharp front end and a sharp rear end, a mounting collar on the needle between its ends and a holder tube extending along an axis and having front and rear ends. According to the invention a piston axially slidable in the holder tube is provided with a mount adapted to fit complementarily with the mounting collar with the needle rear end directed axially back in the tube. The piston normally is at the tube front end with its mount projecting axially forward from the tube. A flexible strand or even a rigid piston has a front end attached to the piston and a rear end projecting from the tube rear end. This mount is fitted into the needle's collar after the blood-collection operation is complete so that a pull on the strand retracts the piston back into the tube carrying the needle fitted to its mount.

With this system, therefore, the possibility of a needlestick caused by trying to poke the used needle back into a small-diameter cap is completely eliminated. All the blood nurse needs to do is fit the holder to the back of the needle and then pull on the strand to retract the needle back into the holder tube where both ends of the needle are effectively protected and the tube can be easily handled and disposed of.

The mount and collar in accordance with the invention are complementary, normally frustoconical sleeves. The tube is cylindrical and the needle rear end is recessed in the collar.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
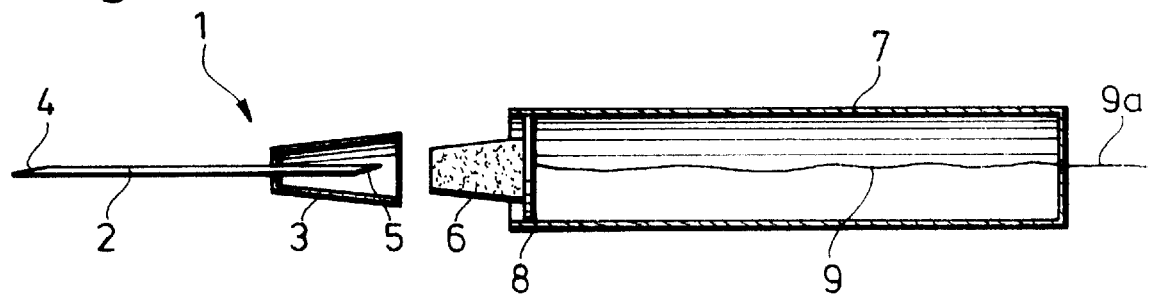
FIG. 1 is an exploded and partly diagrammatic view of the system of this invention.

As seen in FIG. 1 a needle assembly 1 has a needle 2 with a sharpened front end 4 and rear end 5 and fitted between its ends with a frustoconical collar 3. This assembly 1 is normally delivered with a cap covering the portion of the needle 1 projecting from the collar 3; the rear end 5 is recessed in the collar 3.

In use the point 4 is normally inserted into a vein and, once flow through the needle 2 is established, a blood-collection vial or syringe is fitted to the collar 3 with the point 5 piercing the vial's cap. Several such vials can be filled in this way.

A holder tube 7 is basically cylindrical and centered on an axis. It is provided internally with an axially displaceable piston or plug 8 fitted with a forwardly projecting and forwardly frustoconically tapering extension 6 shaped to fit complementarily inside the collar 3, like the top of the blood-collection vial. A flexible thin string 9 is attached to the piston 8, which normally forms a front end wall of the holder tube 7, and has a rear end 9a that hangs out of the rear end of the tube 7. The front end of the tube 7 is turned in to form a rim around a hole 10 and prevent the piston 8 from falling out, and the rear end can even be turned in somewhat to effectively capture it. A cap can be provided for each end of the tube 7 and one of the caps can even be attached to the string 9.

Figure 2:
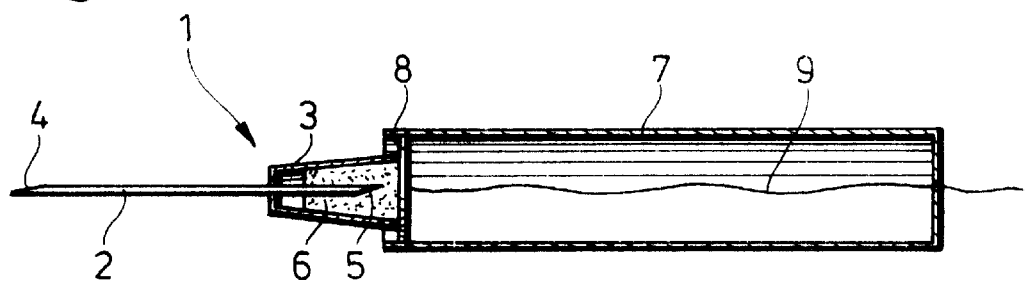
FIG. 2 is an assembled view of the system.
Figure 3:
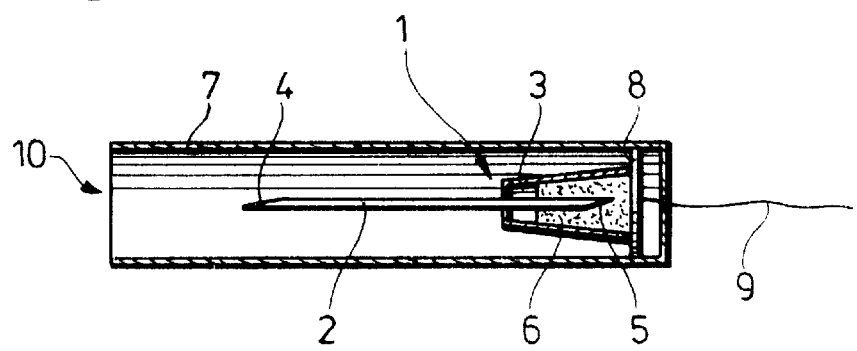
FIG. 3 is a side view showing the assembly ready for disposal.

In use as shown in FIG. 2 the collar 3 is fitted over the extension 6, normally after the blood-collection operation is completed. Then the user pulls on the string 9. This pulls back the piston 8 and attached needle assembly 1 into the position of FIG. 3, with the needle assembly wholly enclosed in the tube 7 whose ends may be capped for further safety. Even if not capped, both ends 4 and 5 of the needle 1 will be completely protected, eliminating the possibility of needlestick on disposal. Either way, the entire assembly of FIG. 3 is disposed of.

We claim:

1. A blood-collection apparatus comprising:

a needle having a sharp front end and a sharp rear end;

a mounting collar fixed on the needle between its ends;

a holder tube extending along an axis and having an open front end and an open rear end;

a plug fitted inside the holder tubes axially slidable in the holder tube, and having a plug mount adapted to fit complementarily to the mounting collar with the mounting collar securely fixed to the plug mount and the needle rear end directed axially back into the holder tube, the plug adapted to be axially slidable in the tube from a front position at the holder tube front end with the plug mount projecting axially forward from the front end of the holder tube to a rear position at the tube rear end; and a strand having a front end attached to the plug and a rear end projecting from the tube rear end, whereby a pull on the strand retracts the plug and the needle fitted thereto to the tube rear end.

2. The blood-collection apparatus defined in claim 1 wherein the mounting collar comprises a frustoconical sleeve and the plug comprises a forwardly projecting frustoconically tapering extension constituting the plug mount and fitting complementarily and securely inside the mounting collar.

3. The blood-collection apparatus defined in claim 1 wherein the strand is flexible.

4. The blood-collection apparatus defined in claim 1 wherein the tube is cylindrical.

5. The blood-collection apparatus defined in claim 1 wherein the needle rear end is recessed in the collar.

6. A method comprising the steps of:

providing a blood-collecting apparatus having a needle having a sharp front end and a sharp rear end, a mounting collar fixed on the needle between its ends, a holder tube extending along an axis and having an open front end and an open rear end, a plug fitted inside the holder tube, adapted to be axially slidable in the holder tube, and having a plug mount adapted to fit complementarily to the mounting collar with the mounting collar securely fixed to the plug mount and the needle rear end directed axially back into the holder tube, the plug being axially slidable in the tube from a front position at the holder tube front end with the plug mount projecting axially forward from the front end of the holder tube to a rear position at the tube rear end, and a strand having a front end attached to the plug and a rear end projecting from the tube rear end, whereby a pull on the strand retracts the plug and the needle fitted thereto to the tube rear end;

using the apparatus to collect blood, thereafter fitting the collar to the plug mount, and thereafter pulling on the strand to retract the plug back into the tube carrying the needle fitted to the plug mount into a rear position with the plug adjacent the rear holder-tube end.

\* \* \* \* \*